United States Patent [19]

Kinast et al.

[11] 4,266,025
[45] May 5, 1981

[54] PRODUCTION OF N-SUBSTITUTED DERIVATIVES OF 1-DESOXY-NOJIRIMYCIN

[75] Inventors: Günther Kinast; Michael Schedel, both of Wuppertal, Fed. Rep. of Germany

[73] Assignee: Bayer Aktiengesellschaft, Leverkusen, Fed. Rep. of Germany

[21] Appl. No.: 97,099

[22] Filed: Nov. 23, 1979

[30] Foreign Application Priority Data

Dec. 12, 1978 [DE] Fed. Rep. of Germany ....... 2853573

[51] Int. Cl.³ .................. C12P 19/26; C12P 17/12
[52] U.S. Cl. ................................. 435/84; 435/122
[58] Field of Search .................... 435/121, 122, 84

[56] References Cited

U.S. PATENT DOCUMENTS 3,998,698  12/1976  Argoudelis et al. ................ 435/122

Primary Examiner—Lionel M. Shapiro
Attorney, Agent, or Firm—Sprung, Felfe, Horn, Lynch & Kramer

[57] ABSTRACT

The invention relates to a process for the production of compounds of the formula

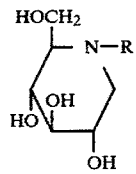
(I)

in which R is hydrogen or optionally substituted alkyl, alkenyl, aralkyl or aryl, by microbiological transformation of

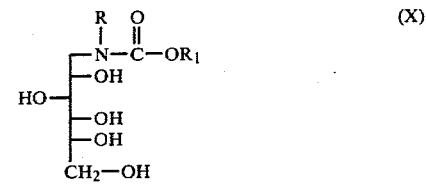
(X)

follow by catalytic hydrogenation. The compounds obtained are useful for the treatment of diabetes, hyperlipoproteinaemia and adiposity which comprises aerobically cultivates, in the presence of an assimilable source of carbon nitrogen, at a temperature of 20° to 45° C. and pH between 2 and 10 and in the presence of an effective amount of a compound of the formula

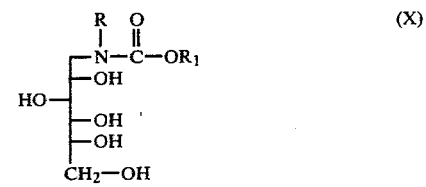
(X)

in which
  R has the above-given meaning and,
  $R_1$ denotes an optionally substituted benzyl radical or an optionally substituted β-alkenyl group, an aerobic microorganism or an extract of aerobic microorganism capable, in a nutrient medium containing a compound of the formula (X), or accumulating an amount of a compound of the formula

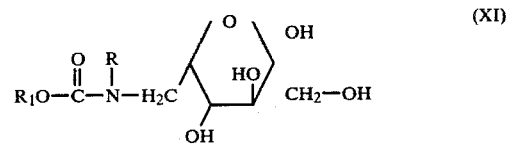
(XI)

in which
  R and $R_1$ have the above-mentioned meanings and
subjecting the resulting compound of the general formula XI to catalytic hydrogenation.

6 Claims, No Drawings

PRODUCTION OF N-SUBSTITUTED DERIVATIVES OF 1-DESOXY-NOJIRIMYCIN

The present invention relates to a new, chemically unobvious process for the production of compounds of the formula

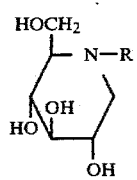

(I)

in which
R denotes a hydrogen atom or an optionally substituted alkyl, alkenyl, aralkyl or aryl group.

Unless otherwise indicated herein in deficiency the term R, alkyl preferably contains 1 to 10 (especially 1 to 6) carbon atoms; alkenyl preferably contains 1 to 10 (especially 2 to 6) carbon atoms; aralkyl is preferably mono- or bi-cyclic carbocyclic hydrocarbon in the aryl portion and preferably contains 1 to 4 (especially 1 to 2) carbon atoms in the alkyl portion; and aryl preferably is mono- or bi-cyclic carbocyclic aryl (such as phenyl, naphthyl or biphenyl).

It has already been disclosed that the compound of the formula (I) in which R denotes a hydrogen atom, known by the name 1-desoxy-nojirimycin, can be obtained either by extraction from plants of the Mors species, according to German Offenlegungsschrift (German Published Specification) No. 2,656,602, or microbiologically with the aid of organisms of the Bacillaceae family, in particular of strain DSM 7, according to German Offenlegungsschrift (German Published Specification) No. 2,658,563. The compounds of the formula (I) can be used as agents for the treatment of diabetes, hyperlipoproteinaemia and adiposity.

It has already been disclosed that 1-desoxynojirimicin can be prepared by hydrogenating the free bases of formula (II) or (III)

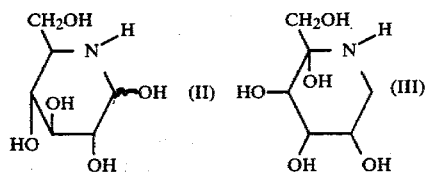

which are not very stable, in accordance with the method of H. Saki and E. Ohki, Chem. Parm. Bull. 16, 2,477 to 2,481 (1968) and H. Paulsen, I. Sangster and H. Heyns, Chem. Ber. 100, 802 to 815 (1967).

The compound of formula (II) used as a starting material in this process is prepared either by converting 5-amino-5-desoxy-1.2-0-isopropylidene-α-D-glucofuranose of formula (IV) into a stable bisulphite adduct of formula (V) by passing sulphur dioxide in for 60 hours, the bisulphite adduct then giving the compound of formula (II) by treatment with barium hydroxide,

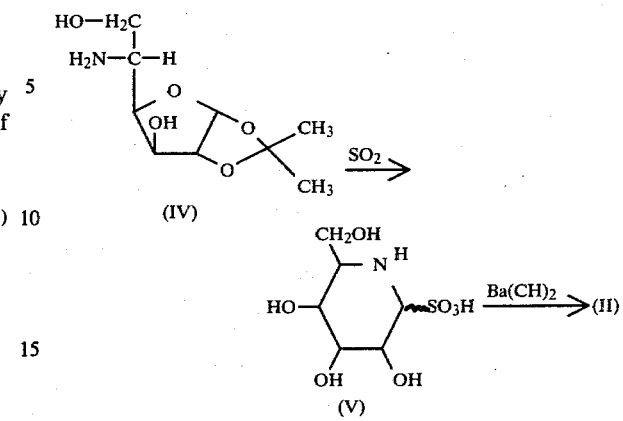

(see German Auslegeschrift (German Published Specification) No. 1,768,044), or by converting the compound of formula (IV) into the trifluoroacetylated derivative of formula (VI), which gives the trifluoroacetyl derivative of formula (VII) by boiling with dilute hydrochloric acid. Subsequent splitting off of the trifluoroacetyl groups gives the compound of formula (II)

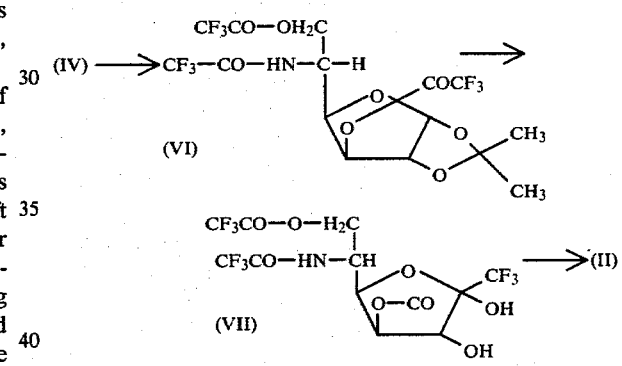

Alternatively, the compound of formula (II) is prepared micro-biologically, starting from glucose (see U.S. Pat. No. 3,998,698).

The compound of formula (III) is obtained from 6-amino-2.3-O-isopropylidene-6-desoxy-α-L-sorbofuranose of formula (VIII) by splitting, and subsequent liberation of the resulting hydrochlorde of formula (IX) by chromatography over an anion exchanger.

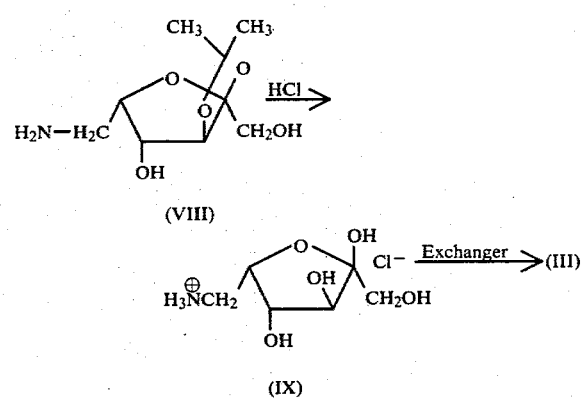

The processes listed here for the preparation of 1-desoxynojirimycin all proceed via several time-consuming stages, and passing through the stage of the unstable compounds of formula (II) and (III) as intermediate products must unavoidably lead to by-products.

In addition, the processes known hitherto for the preparation of the compound of formula (I) in which R denotes hydrogen, in each case require expensive purification steps, such as extraction, column chromatography or chromatography on exchangers, which are partly also necessary because the hydrogenation of the free bases does not proceed stereospecifically.

According to the present invention, there is provided a process for the production of a compound of formula (1), as defined above, in which a compound of the formula

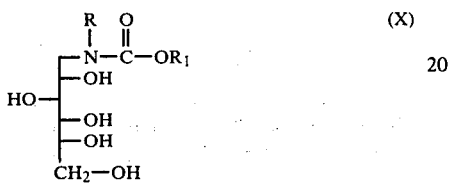

in which

R has the meaning given formula (I) and $R_1$ denotes an optionally substituted benzyl radical or an optionally substituted β-alkenyl group, is reacted microbiologically with an aerobic microorganism or an extract of an aerobic microorganism capable, in a nutrient medium containing a compound of formula (X), of accumulating a compound of the general formula

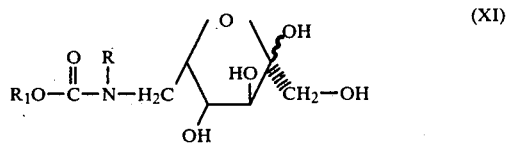

in which

R and $R_1$ have the meaning given above, and subjecting the resulting compound of the general formula (XI) to catalytic hydrogenation. The process of the present invention surprisingly has been found to give compounds of formula (I) in excellent yields.

6-Amino-6-desoxy-L-sorbose (a compound of formula (XI) in which R and $R_1$ denote hydrogen atoms) was hitherto prepared by a purely chemical route from sorbose in an 8-stage synthesis (see H. Paulsen, I. Sangster and K. Heins, Chem. Ber. 100, 802 to 815 (1967)).

In an acid medium, 6-amino-6-desoxy-L-sorbose is present in the furanose form of formula (XIa), and in an alkaline medium in the piperidinose form of formula (XIb), which is in equilibrium with the compound of formula (XIc). Formula (XIb) is identical to formula (III).

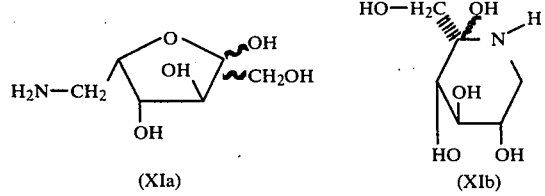

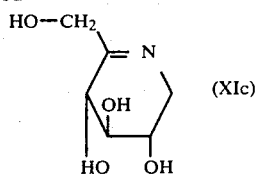

The compounds of formulae (XIa), (XIb) and (XIc) are very unstable and rearrange irreversibly in aqueous solution, especially in the acid pH range, by splitting off water to give the pyridine derivative of the formula (XIII).

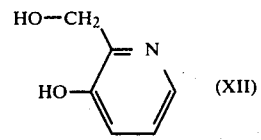

This splitting off of water is further assisted by substituents of the type indicated on the nitrogen, so that, for example, 6-alkylamino-6-desoxy-L-sorboses have not hitherto been disclosed.

It is furthermore known (J. K. N. Jones, M. B. Perry and J. C. Turner, Can. J. Chem. 39, 2,400–2,410 (1961)) that 6-desoxy-6-N-methylacetamido-L-sorbose can be prepared from 1-desoxy-1-N-methylacetamido-D-glucitol in 36% yield by microbiological oxidation for 19 days with Acetobacter suboxidans. The disadvantages of this reaction is on the one hand the long reaction time and on the other hand the fact that the amino group must be protected by acetylation. It is not possible to split off the acetyl group without irreversible, undesired modification (usually decomposition).

It is to be described as exceptionally surprising that the compounds of formula (XI) are obtained in a simple manner in a short time and in high yield by the microbiological/enzymatic process according to the invention, and that these compounds can be hydrogenated smoothly and with good yield to give the compounds of the general formula (I).

The starting compounds of the formula (X) employed in the process according to the invention can be prepared from D-glucose by reductive amination with appropriate amines, hydrogen and nickel, as the catalyst, and subsequent reaction of the products with appropriate chloroformic acid esters.

Microorganisms which are suitable for carrying out the process according to the invention or from which active extracts for carrying out the process according to the invention can be obtained can be procaryotes, that is to say bacteria, or eucaryotes, for example, fungi, and in each case belong to the most diverse taxonomic groups. The expert in the microbiological field can easily find suitable microorganisms by cultivating a relatively large number of aerobic microorganisms or microorganisms which are able to live under aerobic conditions, such as are available, for example, in public collections, in an appropriate nutrient medium which contains a compound of the formula (X), and testing the ability of the microorganisms to catalyse the oxidation reaction according to the invention and to accumulate compounds of the formula (XI).

By having proceeded according to these instructions, it could be found that microorganisms which are suitable for the process according to the invention are, for example, bacteria of the order Pseudomonadales, and within this order, in particular representatives of the Pseudomonadaceae family, and here, above all, bacteria of the Gluconobacter genus. Furthermore, bacteria from the coryneform bacteria group, in particular those of the Corynebaceterium genus, have also proved suitable. Finally, the process according to the invention could also be carried out with fungi, thus, for example, with yeasts of the Endomycetales order, in particular with those of the Spermophthoraceae family, and here principally with representatives of the Metschnikowia genus.

Examples which may be mentioned are: *Gluconobacter oxydans* ssp. *suboxydans* (DSM 50 049), *Glucobacter oxydans* ssp. *suboxydans* (DSM 2003), *Corynebacterium betae* (DSM 20141) and *Metschnikowia pulcherrima* (ATCC 20 515).

The DSM numbers give the numbers under which the microorganisms mentioned are stored in the German Collection of Microorganisms in Göttingen. Metschnikowia pulcherrima is stored in the American Type Culture Collection in Rockville, Maryland, U.S.A.

If the process according to the invention is carried out with intact microorganisms in a growing culture, solid, semi-solid, or liquid nutrient media can be used. Aqueous liquid nutrient media are preferably used.

The microorganisms can be cultured in all nutrient media which are known to be used for culturing microorganisms of the abovementioned groups and which contain the compound of the formula (X) to be oxidised in the process according to the invention. The nutrient medium must contain sources of carbon and nitrogen which can be assimilated, and mineral salts. Suitable sources of carbon and nitrogen which can be assimilated are, above all, complex mixtures such as in particular, biological products of different origin, for example soya bean flour, cottonseed flour, lentil flour, pea flour, soluble and insoluble vegetable proteins, corn-steep liquor, yeast extract, peptones and meat extract. Possible sources of nitrogen are, in addition, ammonium salts and nitrates, for example ammonium chloride, ammonium sulphate, sodium nitrate and potassium nitrate. The mineral salts which the nutrient medium should contain supply, for example, the following ions: $Mg^{++}$, $Na^+$, $K^+$, $Ca^{++}$, $NH_4^+$, $Cl^-$, $SO_4^{--}$, $PO_4^{---}$ and $NO_3^-$, and ions of the customary trace elements, such as Cu, Fe, Mn, Mo, Zn, Co and Ni.

If these salts or trace elements are not present to a sufficient extent in the complex nutrient medium constituents mentioned or in the water used, it is appropriate to supplement the nutrient medium correspondingly.

It has been found that a considerable shortening of the time necessary for complete reaction of compounds of formula (X) to give those of formula (XI) is made possible by adding compounds of intermediate metabolism and other cell constituents to the medium, thus, for example, aminoacids or compounds from the tricarboxylicacid cycle.

The compound of the formula (X) to be oxidised in the process according to the invention can be added to the base nutrient medium either by itself or as a mixture with one or more oxidisable compounds. Additional oxidisable compounds which can be used are primary alcohols, for example ethanol, secondary alcohols, for example isopropanol, polyols, for example sorbitol or glycerol, aldehydes, for example glycol-aldehyde, aldoses, for example glucose, or gluconic acids.

If one or more of the compounds mentioned are added to the nutrient solution, the compound of the formula (X) to be oxidised can be added either before inoculation or at any other desired later point in time between the earlier lag phase and the later stationary growth phase. In such a case, the organism concerned is precultivated on the particular oxidisable compounds added.

A pH range of between 2 and 10 is suitable for the process according to the invention. It is favourable to buffer the culture in this range, for example with phosphate buffer or acetate buffer.

As is customary in fermentation technology, automatic regulation of the pH can also be effected, in which a sterile organic or inorganic acid, for example sulphuric acid, or a sterile aqueous alkali, for example sodium hydroxide solution, is injected into the culture solution at intervals of time.

As is general in the case of microbiological processes, foreign infections of the culture media should be avoided. For this, the customary measures are taken, such as sterilisation of the nutrient media, the culture vessels and the air necessary for the aeration. Steam sterilisation and also dry sterilisation, for example, can be used to sterilise the culture vessels; the air and the culture media can likewise be sterilised by steam, but also by filtration.

The nutrient media are inoculated by generally customary methods, for example via cultures in small slanting tubes or in flasks.

The culture is produced under aerobic conditions and can be obtained by the generally customary methods, for example using shaken cultures, for example in shaken flasks, cultures agitated by air or submersed cultures. The culture is preferably produced by the aerobic submersion process in aerated fermenters, for example in customary submersion fermentation tanks. It is possible to produce the culture continuously or discontinuously. The discontinuous procedure is preferred.

It is appropriate to ensure that the microorganisms are brought into sufficient contact with oxygen and the nutrients. This can be effected by the generally customary methods, such as shaking and stirring.

If foam is formed in an undesired amount during the culturing, the customary chemical anti-foaming agents, for example liquid fats and oils, oil-in-water emulsions, paraffins, higher alcohols, such as octadecanol, silicone oils or polyoxyethylene or polyoxypropylene compounds, can be added. Foam can also be suppressed or removed with the aid of the customary mechanical devices.

The growing temperature can be between 20 and 45° C. The growing time can be varied greatly, the composition of the nutrient medium and the growing temperature, for example, being of importance.

The particular optimum conditions can easily be established by any expert in the microbiological field.

It has been found that for complete reaction of the compounds of the formula (X) added to the culture broth, an incubation time of between 3 hours and 7 days after the addition is in general necessary.

It is also possible to carry out the oxidation reaction according to the invention with concentrated cell suspensions of suitable microorganisms. Concentrated cell suspensions are prepared as follows: a culture of the microorganisms in question is produced in a suitable nutrient solution, and the microorganisms are then harvested, for example by centrifugation, and suspended in a smaller volume of the same nutrient solution or in salt solutions or buffer solutions, for example physiological sodium chloride solution or aqueous solutions of $KH_2PO_4$, Na acetate or maleate, or simply in tap water or distilled water. Compounds of the formula (X) are then added to such a cell suspension and the oxidation reaction according to the invention is carried out under the conditions described above for growing cultures.

The advantages of this process is the shortening of the reaction time of the process according to the invention to a few hours which is made possible by the higher concentration of microorganisms.

It is furthermore possible to carry out the process according to the invention not only with growing cultures of microorganisms or with concentrated cell suspensions obtained therefrom, but also with extracts or extract fractions prepared from these bacteria. These extracts can be crude extracts, such as are obtained by conventional disintegration of microorganism cells. Disintegration methods which can be used are: ultrasonic treatment, passage through a French pressure cell, grinding with quartz sand, incubation with lysing enzymes, antolysis or repeated freezing and thawing.

If non-fractionated crude extracts are used for oxidising compounds of the formula (X) to compounds of the formula (XI), in principle the same reaction conditions such as have been described for carrying out the process according to the invention with growing or dormant microorganism cells have proved favourable.

If the process according to the invention is to be carried out with partly purified extract preparations (enzymes), the generally customary methods of protein chemistry can be used to obtain such preparations, such as ultracentrifugation, precipitation reactions, ion exchange chromatography or adsorption chromatography, gel filtration or electrophoretic methods. To clarify the question of which of several fractions obtained by one of the methods mentioned is suitable for catalysing the oxidation reaction according to the invention, an aliquot of this fraction is mixed with compounds of the formula (X) at a temperature between 20° and 45° C. and at a pH between 2 and 10 and the batch is investigated by thin layer chromatography with regard to the formation of compounds of the formula (XI). To carry out the reaction according to the invention with fractionated cell extracts, it may be necessary that additional reaction components have to be added to the batch, for example physiological or synthetic electron acceptors, such as $NAD^+$, $NADP^+$, methylene blue, dichlorophenolindophenol and tetrazolium salts. If such additional reaction components have to be added, these can be employed either in substrate amounts, that is to say in concentrations which correspond to that of the compound of the formula (X) employed, or in catalytic amounts, that is to say in concentrations which are significantly below the chosen concentration of the compound of the formula (X).

If, in the second case, it is intended to ensure that the process according to the invention is carried out approximately quantitatively, a system which continuously regenerates the reactant which is present only in a catalytic amount must also be added to the reaction batch. This system can be, for example, an enzyme which ensures that an electron acceptor reduced in the course of the reaction according to the invention is reoxidised in the presence of oxygen or other oxidising agents.

In other respects, the same conditions as have been cited above for the oxidation of compounds of formula (X) to compounds of the formula (XI) in growing microorganism cultures or concentrated cell suspensions have also proved advantageous for carrying out the process according to the invention with fractioned cell extracts. In particular, in this case also the temperature range is 20° to 45° C. and the pH range is 2 to 10. However, the amount of the compounds of the formula (XI) formed reaches its maximum within a relatively short period. Depending on the extract concentration, an incubation time of between 2 hours and 3 days suffices.

The time-dependent formation of the compound of the formula (XI) in the culture medium can be followed by thin layer chromatography.

The compounds of the formula (XI) which are obtained according to the invention are isolated from the culture solution, and converted to the compounds of the formula (I) according to the invention, preferably as follows.

The culture solution is extracted with a suitable solvent, optionally after evaporating off a portion of the water in vacuo and centrifuging off or filtering off the cell masses. Suitable solvents are, inter alia, higher in alcohols, for example alkanols with 4 or more carbon atoms, such as butanol; ketones, for example alkyl ketones with 4 or more carbon atoms, such as methyl isobutyl ketone, alkyl esters of alkanoic acids in which the alkyl portion contains 1 to 6 carbon atoms and the alkanoic acid is one having 1 to 6 carbon atoms, ethyl acetate or mixtures of the above higher alcohols with non-polar solvents, such as butanol/toluene mixtures. It is also possible to evaporate the culture solution to dryness in vacuo and to take up the compounds, according to the invention, of the formula (XI) from the residue using alcohols, for example $C_1$–$C_4$-alkanols, such as methanol, ethanol and propanol, or the abovementioned solvents. The compounds, according to the invention, of the formula (XI) can be obtained in the pure form from the extracts thus obtained, by evaporating and optionally after recrystallisation from a suitable solvent, such as water or ethanol.

In order to prepare the compounds, according to the invention, of the formula (I), the compounds of the formula (XI) are hydrogenated, the reaction preferably being carried out in the customary inert inorganic or organic solvents, such as water, alcohols, glacial acetic acid or corresponding solvent mixtures. By choosing the suitable pH, especially at a pH of between 0 and 7, and by choosing the suitable solvent or solvent mixture, such as methanol/water, the gluco-configuration on C-5 of the compounds, according to the invention, of the formula (I) is obtained selectively. The pH can be adjusted to the suitable value using the customary mineral acids, such as hydrochloric or sulphuric acid, or using organic acids, such as acetic acid or oxalic acid. The catalysts used are the customary noble metal catalysts, such as Pd, Pt, or Ni. The gluco-configuration is obtained stereoselectively in particular in the case of hydrogenation with Pd in water.

The reaction temperature can be between $-30$ and $+120°$ C. and the reaction is preferably carried out at room temperature.

It is also possible to hydrogenate the culture solutions direct, analogously to the procedure indicated above, using a suitable noble metal such as Raney nickel, without prior isolation of the compounds, according to the invention, of the formula (XI), optionally after evaporating off a portion or all of the water, centrifuging off or filtering off the cell masses, clarifying with active charcoal and stirring thoroughly.

The compounds, according to the invention of the formula (I) are isolated, after separating off the catalyst, by evaporating off the solvent, and in some cases salts of the compounds of the formula (I) with the acids used for the hydrogenation or with carbonic acid are obtained. These salts can be isolated directly and optionally purified by recrystallisation; alternatively the salts are converted by means of a suitable organic base, such as triethylamine, or $Ba(OH)_2$ or especially by means of an anion exchange resin to the free bases of the formula (I), which can optionally be purified by recrystallisation from a suitable solvent, such as ethanol/water. In order to separate off relatively large amounts of inorganic salts or substances from the nutrient medium from the culture solution, it can be advantageous, especially if the compounds of the formula (XI) have not been isolated as the pure substance and the culture solution is hydrogenated direct, to pass the solution obtained after the hydrogenation reaction through an acid ion exchanger and the elute the compounds of the formula (I), bound to the ion exchanger, with aqueous or alcoholic ammonia solution. After evaporating to dryness and optionally after recrystallization, the pure compounds of the formula (I) are obtained.

Preferably, R denotes a hydrogen atom, a $C_1$ to $C_{10}$ (preferably $C_1$ to $C_6$)alkyl group which is optionally substituted by OH, $C_1$ to $C_4$-alkoxy, $C_1$-$C_4$-alkylamino or di($C_1$ to $C_4$ alkyl)-amino, or a $C_2$ to $C_{10}$-$\beta$-alkenyl group, preferably a $C_2$ to $C_4$-$\beta$-alkenyl group.

$R_1$ preferably denotes a benzyl radical which is optionally substituted by chlorine, bromine, nitro, methyl or methoxy, or denotes an allyl group.

Very particularly preferentially, R denotes a hydrogen atom or a $C_1$ to $C_{10}$ (preferably $C_1$ to $C_6$) alkyl, hydroxyethyl or allyl group and $R_1$ denotes a benzyl or allyl group.

The preparation of compounds of formula (I) by the process of the present invention is illustrated in the following Examples.

EXAMPLE 1

Preparation of 1-desoxynojirimycin by oxidation of 1-benzyloxycarbonylamino-1-desoxy-D-glucitol by Gluconobacter oxydans ssp. suboxydans in a growing culture in a shaking flask and subsequent hydrogenation of the 6-benzyloxycarbonylamino-6-desoxy-L-sorbose formed.

*Gluconobacter oxydans* ssp. *suboxydans* (DSM 50049) is pre-cultivated in a liquid nutrient solution which contains, per liter, 20 g of yeast extract, 200 g of sorbitol and 10 g of $KH_2PO_4$ dissolved in dimineralised water. The pH value of the nutrient solution for the pre-culture is adjusted to 6.2 and 100 ml portions of the solution are introduced into 1 liter conical flasks and sterilised by heating for 15 minutes at 121° C. in an autoclave. The oxidation of benzyloxycarbonyl-protected 1-amino-1-desoxy-D-glucitol is carried out in a nutrient solution which contains, per liter, 20 g of yeast extract, 200 g of sorbitol, 10 g of $KH_2PO_4$ and 20 g of benzyloxycarbonyl-protected 1-amino-1-desoxy-D-glucitol dissolved in tap water. The pH value is adjusted to 6.2. 100 ml portions of the nutrient solution are introduced into 1 liter conical flasks and sterilised by heating for 15 minutes at 121° C. in an autoclave. After cooling, each flask is inoculated with, in each case, 2 ml of the pre-culture and then incubated at 36° C. on a shaking machine at 280 revolutions per minute. The formation of benzyloxycarbonyl-protected 6-amino-6-desoxy-L-sorbose is followed by thin layer chromatography. Complete conversion is achieved after 4 days. The culture broths of 3 batches carried out in parallel are combined, so that a volume of 300 ml is available for working up.

The culture solution was centrifuged and extracted three times with, in each case, 100 ml of n-butanol/toluene, 1:1. The extract was evaporated in vacuo, the residue was taken up in 40 ml of $H_2O$ and 60 ml of methanol, 10 ml of 2 N HCl and 0.5 g of Pd/C (5%) were added and the mixture was hydrogenated for 5 hours, whilst stirring. The catalyst was then filtered off, the solution was rendered alkaline with a basic ion exchanger, the solvent was evaporated in vacuo and the residue was recrystallised from water/ethanol. Yield: 1.1 g of 1-desoxynojirimycin (melting point 197°–199° C.).

EXAMPLE 2

Preparation of 1-desoxy-nojirimycin.

*Glucobacter oxydans* ssp. *suboxydans* (DSM 2003) was pre-cultivated in a liquid nutrient solution which contained, per liter, 20 g of yeast extract, 100 g of sorbitol and 10 g of $KH_2PO_4$ dissolved in tap water. The pH value of the nutrient solution was adjusted to 6.2 and the solution was sterilised in an autoclave by heating for 20 minutes at 121° C. The oxidation of benzyloxycarbonyl-protected 1-amino-1-desoxy-D-glucitol was carried out in a nutrient solution with an initial pH value of 6.2, which contained, per liter, 20 g of the said substance and also 20 g of yeast extract, 100 g of sorbitol, 10 g of $KH_2PO_4$, 10 g of leucine and 5 g of isoleucine. 250 ml of this solution were introduced into a 1 liter conical flask and treated for 20 minutes at 121° C. in an autoclave. The solution was inoculated with a well-grown pre-culture, to give a 5% concentration of the pre-culture, and incubated at 36° C. and 280 rpm on a rotary shaking machine. The formation of the oxidation product was followed by thin layer chromatography. Complete conversion was achieved after 3 days.

3 liters of the culture solution thus obtained were concentrated to 1 liter in vacuo and the solution was extracted 3 times by covering with a layer of 500 ml of butanol/toluene, 10:1, and stirring the lower phase. The extract was evaporated to dryness in vacuo and the residue was recrystallised from water. 51 g of 6-benzyloxycarbonylamino-6-desoxy-L-sorbose were obtained and this was hydrogenated in 800 methanol, 800 ml of water and 80 ml of HCl with 2 g of Pd/C (5%) under a pressure of 5 atmospheres. The catalyst was filtered off and the solution was passed through a strongly acid ion exchanger (Lewatit TSW 40), rinsed with water and eluted with 0.5 N $NH_3$ solution. After evaporating the eluate, the residue was recrystallised from water/ethanol. 19 g of 1-desoxynojirimycin were obtained.

EXAMPLE 3

Preparation of 1-desoxynojirimycin.

The micro-organism *Metschnikowia pulcherrima* (ATCC 20515) was pre-cultivated in small slanted tubes on a medium which contained, per liter, 3 g of yeast extract, 6 g of peptone, 10 g of glucose, 8 g of NaCl and 20 g of agar in demineralised water. This pre-culture was used to inoculate 250 ml of a liquid medium (in a 1 liter conical flask) which contained, per liter, 3 g of yeast extract, 6 g of peptone, 10 g of sorbitol, 8 g of NaCl and 10 g of benzyloxycarbonyl-protected 1-amino-1-desoxy-D-glucitol dissolved in demineralised water and had been sterilised in an autoclave by heating for 20 minutes at 121° C. The culture was incubated at 35° C. on a rotary shaking machine at 200 rpm. The content of benzyloxycarbonyl-protected 6-amino-6-desoxy-L-sorbose in the culture broth was determined by thin layer chromatography. After 2 days 4 g/l (40%) has been converted. The fermentation was discontinued at this point in time and the culture solution was worked up as indicated in Example 2. It was possible to obtain the 6-benzyloxycarbonylamino-6-desoxy-L-sorbose in the pure form by recrystallisation from water and from ethanol and to hydrogenate it to 1-desoxynojirimycin as indicated in Example 1.

EXAMPLE 4

Preparation of 1-desoxynojirimycin

The micro-organism *Corynebacterium betae* (DSM 20141) was pre-cultivated in small slanted tubes which contained the following nutrient media: 10 g/l of tryptically digested casein-peptone, 6 g/l of yeast extract, 5 g/l of sorbitol, 5 g/l of NaCl and 20 g/l of agar in demineralised water. A small slanted tube with a good growth was used to inoculate 250 ml of a liquid nutrient solution (in a 1 liter conical flask) which contained, per liter, 10 g of tryptically digested casein-peptone, 5 g of yeast extract, 5 g of sorbitol, 5 g of NaCl and 10 g of benzyloxycarbonyl-protected 1-amino-1-desoxy-D-glucitol. The constituents of the nutrient medium were dissolved in demineralised water and sterilised by heating for 20 minutes in an autoclave at 121° C. The culture was incubated at 37° C. on a rotary shaking machine at 200 rpm. The content of benzyloxycarbonyl-protected 6-amino-6-desoxy-L-sorbose was determined by thin layer chromatography. After 2 days, 3 g/l (corresponding to 30%) had been converted. The fermentation was discontinued at this point in time, the cells were separated off by centrifuging and the clear supernatent liquor from the culture was worked up as indicated in Example 3.

EXAMPLE 5

Preparation of 1-desoxynojirimycin by oxidation of benzyloxycarbonyl-protected 1-amino-1-desoxy-D-glucitol by *Glucobacter oxydans* ssp. *suboxydans* in a growing culture in a fermenter and subsequent hydrogenation of the benzyloxycarbonyl-protected 6-amino-6-desoxy-L-sorbose formed.

*Glucobacter oxydans* spp. *suboxydens* (DMS 2003) was pre-cultivated in small slanting tubes. The nutrient medium contained, per liter, 10 g of yeast extract, 100 g of sorbitol and 2 g of $KH_2PO_4$, dissolved in tap water. A liquid culture of 250 ml of the same medium, but without agar, in a 1 liter conical flask was inoculated with a small tube with a good growth and incubated overnight at 36° C. on a rotary shaking machine at 280 rpm. This 2nd pre-culture was used to inoculate a 10 liter fermenter which was charged with a liquid medium which contained, per liter, 10 g of yeast extract, 100 g of sorbitol, 2 g of $KH_2PO_4$ and 10 g of benzyloxycarbonyl-protected 1-amino-1-desoxy-D-glucitol. The pH value had been adjusted to 6.2. The medium had been sterilised by heating for 15 minutes in an autoclave at 121° C. 5 liters of air per minute were blown through the fermenter and the fermenter was stirred at 500 rpm. The incubation temperature was 36° C. Samples were taken under sterile conditions at various times and the content of benzyloxycarbonyl-protected 6-amino-6-desoxy-L-sorbose was determined by thin layer chromatography. Complete conversion was achieved after 2½ days.

The culture solution was concentrated to 2 liters in vacuo, the precipitate which had separated out was brought back into solution by warming to 60°–80° C. and the turbid solution was stirred with active charcoal and filtered. 6-Benzyloxycarbonylamine-6-desoxy-L-sorbose precipitated from the filtrate and was recrystallised once from water and once from ethanol. Yield 90 g. The product was hydrogenated in the customary manner to give 1-desoxynojirimycin.

EXAMPLE 6

Preparation of 1-desoxynojirimycin

*Glucobacter oxydans* ssp. *suboxydans* (DSM 2003) was cultivated on a 10 liter scale in a fermenter in a medium (initial pH value: 6.2) which contained, per liter, 100 g of sorbitol, 20 g of yeast extract and 2 g of $KH_2PO_4$-dissolved in tap water. 5 liters of air per minute were blown through the fermenter and the latter was stirred at 500 rpm and kept at a temperature of 36° C. After incubation for 10 hours, the cells were centrifuged off from the culture broth and suspended in 1 liter of a medium which contained 20 g of yeast extract, 2 g of $KH_2PO_4$ and 20 g of benzyloxycarbonyl-protected amino-1-desoxy-D-glucitol. This 10-fold concentrated cell suspension was incubated in a 1 liter fermenter at 36° C., 5 liters of air per minute were blown through and the suspension was stirred at 500 rpm. Complete conversion was achieved after 24 hours. The cells were centrifuged off and the supernatent liquor was worked up, and hydrogenated to 1-desoxynojirimycin, as indicated in Example 1.

EXAMPLE 7

Preparation of 1-desoxynojirimycin

*Glucobacter oxydans* ssp. *suboxydans* (DSM 2003) was pre-cultivated on a 10 liter scale in a fermenter in a medium which contained, per liter, 100 g of sorbitol, 20 g of yeast extract and 2 g of $KH_2PO_4$-dissolved in tap water. 5 liters of air per minute were blown through the fermenter and the latter was stirred at 500 rpm and kept at a temperature of 36° C. After incubation for 16 hours, the cells were centrifuged off from the culure broth, washed once by suspending in 10 mM $KH_2PO_4$ and centrifuging again and then suspended in 300 ml of 10 mM $KH_2PO_4$. The cell suspension thus obtained was disintegrated by two passes through a French pressure cell under 8 bars. The cell-free extract was introduced into a 1 liter conical flask, benzyloxycarbonyl-protected 1-amino-1-desoxy-D-glucitol was added until the concentration was 20 g/l and the mixture was incubated at 36° C. on a rotary shaking machine at 280 rpm.

Complete conversion was achieved after 17 hours. The culture solution (300 ml) was worked up as in Example 1. After hydrogenation, 1.8 g of 1-desoxynojirimycin were obtained.

EXAMPLE 8

Preparation of 1-desoxynojirimycin by oxidation of benzyloxycarbonyl-protected 1-amino-1-desoxy-D-glucitol in a defined enzyme reaction in a cell-free extract of *Glucobacter oxydans* ssp. *suboxydans* and subsequent hydrogenation of the benzyloxycarbonyl-protected 6-amino-6-desoxy-L-sorbose formed.

A cell-free extract of *Glucobacter oxydans* ssp. *suboxydans* was prepared as indicated in Example 6. The following were added to the extract: niconic acid amide-adenine-dinucleotide phosphate in the form of the Na salt (NADP) to give a final concentration of 0.2 mM. a microsomal crude fraction of the yeast Saccharomyces cerevisiae (ATCC 287) (1 mg/ml), as the NADP-regenerating system, and 1-benzyloxy-carbonyl-protected 1-amino-1-desoxy-D-glucitol (10 g/l).

The mixture was incubated at 36° C. in a waterbath and oxygen was blown through it. The formation of benzyloxycarbonyl-protected 6-amino-6-desoxy-L-sorbose was measured by thin layer chromatography. After 13 hours, a content of 7 g of 6-amino-6-desoxy-L-sorbose per liter, was detectable-corresponding to a 70% conversion. The reaction was discontinued at this point in time and the mixture was worked up as indicated in Example 3 and the resulting 6-benzyloxycarbonylamino-6-desoxy-L-sorbose was hydrogenated to 1-desoxynojirimycin.

EXAMPLE 9

Preparation of 1-desoxy-N-methylnojirimycin by oxidation of benzyloxycarbonyl-protected N-methyl-1-amino-1-desoxy-D-glucitol by *Glucobacter oxydans* ssp. *suboxydans* in a growing culture in a shaking flask and subsequent hydrogenation of the benzyloxycarbonyl-protected N-methyl-6-amino-6-desoxy-L-sorbose formed.

*Glucobacter oxydans* ssp. *suboxydans* were precultivated as described in Example 2. The oxidation reaction was carried out as described in that example, except that, in place of the benyloxycarbonyl-protected 1-amino-1-desoxy-D-glucitol, the corresponding N-methyl compound was added to give a concentration of 20 g/l. 100% conversion was achieved after 4 days.

300 ml of the culture solution were worked up by centrifuging off the cell masses and extracting the clear solution 3 times with, in each case, 100 ml of n-butanol/toluene, 10:2, evaporating the extract in a rotary evaporator and twice recrystallising the residue from water. 5.5 g of 6-desoxy-N-benzyloxycarbonyl-6-methylamino-L-sorbose were obtained and this was hydrogenated under the customary conditions to give 1-desoxy-N-methylnojirimycin. 2.1 g of 1-desoxy-N-methylnojirimycin with a melting point of 152° C. (ethanol) were obtained.

EXAMPLE 10

Preparation of 1-desoxynojirimycin by oxidation of 1-benzyloxycarbonylamino-1-desoxy-D-glucitol by *Gluconobacter oxydans* ssp. *suboxydans* in a shaken flask and subsequent hydrogenation of the 6-benzyloxycarbonylamino-6-desoxy-1-sorbose formed.

*Gluconobacter oxydans* ssp. *suboxydans* (DSM 50049) was pre-cultivated in a liquid nutrient solution which contained, per liter, 20 g of yeast extract, 200 g of sorbitol and 10 g of $KH_2PO_4$ dissolved in demineralised water. The pH value of the nutrient solution was adjusted to 6.2 and 250 ml portions of the solution were introduced into 1 liter conical flasks, sterilised by heating for 15 minutes in an autoclave at 121° C. and, after cooling, inoculated with a pre-culture cultivated in the same medium, to give a 2% concentration of the said pre-culture. Incubation was carried out on a rotary shaking machine at 28° C. and 280 rpm.

After 36 hours, 25 ml of hot 20% strength solution, at 70°-90° C., of benzyloxycarbonyl-protected 1-amino-1-desoxy-D-glucitol in distilled water were added to each flask. This solution had been sterilized by heating beforehand in an autoclave (5' at 105° C.). The flasks were then further incubated at 28° C. and 280 rpm. The formation of benzyloxycarbonyl-protected 6-amino-6-desoxy-L-sorbose was followed by thin layer chromatography. Complete conversion was achieved after 2 days. At this point in time and after a further 2 days, the feeding with benzyloxycarbonyl-protected 1-amino-1-desoxy-D-glucitol was twice repeated in the same way. Complete conversion was achieved after 8 days. The culture broths from 3 batches carried out in parallel were combined, so that a volume of 750 ml was available for working up.

The culture solution was stored for 3 days at 0° to 5° C., the precipitate which had crystallised out was separated off and dissolved in 500 ml of methanol, the insoluble cell residues were centrifuged off and the clear solution was evaporated. The resulting crystalline product was recrystallised once from isopropanol. 40 g of 6-benzyloxycarbonylamino-6-desoxy-L-sorbose were obtained (melting point 107°-111° C.). In order to convert it to 1-desoxynojirimycin, the substance was dissolved in 500 ml of methanol, the solution was added to 0.4 g of $K_2CO_3$ and 10 g of 5% Pd/C in 1 liter $H_2O$ and the mixture was hydrogenated for 3 hours under 80 atmospheres of $H_2$ and at 50°-60° C. After filtering off the catalyst, the batch was evaporated to dryness in vacuo and the residue was recrystallised from methanol.

Yield 16 g, melting point 202°-205° C.

EXAMPLE 11

Preparation of 1-desoxynojirimycin by oxidation of 1-allyloxycarbonylamino-1-desoxy-D-glucitol by *Glucobacter oxydans* ssp. *suboxydans* in a shaken flask and subsequent hydrogenation of the 6-allyloxycarbonylamino-6-desoxy-L-sorbose.

*Glucobacter oxydans* ssp. *suboxydans* (DSM 2003) was pre-cultivated as described in Example 10 in 250 ml of a nutrient solution which contained yeast extract and sorbitol. After 2 days, 25 ml of a 10% strength solution of allyl-protected 1-amino-1-desoxy-D-glucitol, which had been sterilised beforehand by heating in an autoclave (5 minutes at 105° C.), were added. The conversion was followed by means of thin layer chromatography. It was quantitative after 36 hours. At this point in time, the fermentation was discontinued, the culture solution was concentrated to 100 ml in vacuo and extracted 3 times with, in each case, 50 ml of butanol, the extract was evaporated and the residue was chromatographed on 200 g of silica gel using ethyl acetate/methanol/water, 10:3:2. After recrystallisation from acetonitrile, 1.3 g of 6-allyloxycarbonylamino-6-desoxy-L-sorbose were obtained and this was dissolved in 10 ml of water and hydrogenated at 50°-60° C. and under 80 atmospheres in the presence of 1 g of 10% strength Pd-on-charcoal for 8 hours. After filtering off the catalyst, evaporating the solution and recrystallising the residue from methanol, 0.7 g of 1-desoxynojirimycin was obtained.

EXAMPLE 12

Preparation of 1-desoxy-N-methylnojirimycin by oxidation of 1-benzyloxycarbonylamino-1-desoxy-N-methyl-D-glucitol by *Glucobacter oxydans* ssp. *suboxy-*

*dans* in a shaken flask and subsequent hydrogenation of the 6-benzyloxycarbonylamino-6-desoxy-N-methyl-L-sorbose formed.

*Glucobacter oxydans* ssp. *suboxydans* (DSM 2003) was pre-cultivated as described in Example 10 in 250 ml of a nutrient solution which contained yeast extract and sorbitol. After 2 days, 25 ml of a hot 10% strength solution, at 70°–90° C., of 2.5 g of 1-benzyloxycarbonylamino-1-desoxy-N-methyl-D-glucitol in distilled water, which had been sterilised beforehand by heating in an autoclave (5 minutes at 105° C.), were added. The conversion was followed by means of thin layer chromatography. It was quantitative after 36 hours. At this point in time, the fermentation was discontinued, the contents of 10 flasks, having a total volume of 2.5 liters, were added together, concentrated to 0.5 liters in vacuo and stored for 3 days at 0° to 5° C. The precipitate which had crystallised out was filtered off and twice recrystallised from water. 13 g of 6-benzyloxycarbonylamino-1-desoxy-N-methyl-L-sorbose with a melting point of 105°–107° C. were obtained. In order to convert it to 1-desoxy-N-methylnojirimycin, the substance was dissolved in 150 ml of methanol, 300 ml of $H_2O$, 0.4 ml of 10% strength $K_2CO_3$ solution and 5 g of 5% strength Pd-on-charcoal were added and the mixture was hydrogenated for 3 hours under 80 atmospheres and at room temperature. After filtering off the catalyst, the batch was evaporated and the residue was recrystallised from ethanol/water. Yield: 6 g of 1-desoxy-N-methylnojirimycin, melting point 151°–3° C.

EXAMPLE 13

Preparation of 1-desoxy-N-hydroxyethylnojirimycin by oxidation of benzyloxycarbonyl-protected 1-(2-hydroxy-ethyl-amino)-1-desoxy-D-glucitol by *Glucobacter oxydans* ssp. *suboxydans* in a fermenter and subsequent hydrogenation of the benzyloxycarbonyl-protected 1-(2-hydroxyethylamino)-6-desoxy-L-sorbose formed.

*Glucobacter oxydans* ssp. *suboxydans* was precultivated in a 10 liter fermenter in a medium which contained 5% of sorbitol, 2% of yeast extract, 0.4% of $KH_2PO_4$ and 0.04% of polyol anti-foam and had been sterilised for 45 minutes at 121° C. in an autoclave. After 24 hours, 500 ml of a 20% strength solution of benzyloxycarbonyl-protected 1-(2-hydroxyethylamino)-1-desoxy-D-glucitol in distilled water were fed into the culture. The solution had been sterilised by sterile-filtration. The feeding was repeated on the 2nd and on the 3rd day. On the 4th day, the entire substrate had been converted. The fermentation was discontinued at this point in time, the culture solution was evaporated to dryness in vacuo, the residue was stirred thoroughly 3 times with, in each case, 1 liter of ethanol, the ethanol phase was evaporated and the residue was purified on 1 kg of silica gel using ethyl acetate/metanol/water, 10:3:2. The resulting 6-benzyloxycarbonyl-6-desoxy-N-(2-hydroxyethyl)-L-sorbose (180 g) was hydrogenated analogously to Example 10 and the resulting 1-desoxy-N-hydroxyethylnojirimycin was recrystallised from ethanol/water or methylglycol.

Yield: 70 g, melting point 141°–3° C.

EXAMPLE 14

Preparation of 1-benzyloxycarbonylamino-1-desoxy-D-glucitol:

Benzyloxycarbonyl chloride was added dropwise to 3.7 kg of 1-amino-1-desoxy-D-glucitol (about 70% pure) in 7 liters of $H_2O$, whilst stirring vigorously, and the pH was kept at 8–9 with 2 N sodium hydroxide solution. The batch was allowed to warm to 40°–50° C. during this operation. The batch was then further stirred overnight at room temperature and the precipitate was filtered off, washed with acetone and recrystallised from water.

Yield 3 kg, melting point 143°–5° C.

EXAMPLE 15

Preparation of 1-benzyloxycarbonylamino-1-desoxy-N-methyl-D-glucitol:

Prepared analogously to Example 16 from 1-methylamino-1-desoxy-D-glucitol, recrystallised from ethanol. Melting point 123°–5° C.

EXAMPLE 16

Preparation of 1-allyloxycarbonylamino-1-desoxy-D-glucitol and allyloxycarbonyl chloride. For working up, the batch was extracted with ethyl acetate, desalinated through a mixed bed ion exchanger and evaporated and the residue was recrystallised from ethanol.

Melting point 99°–102° C.

EXAMPLE 17

Preparation of 1-benzyloxycarbonylamino-1-desoxy-N-(2-hydroxyethyl)-D-glucitol. Analogous to Example 16, compound which is difficult to recrystallise.

We claim:

1. A process for the production of a compound of the formula

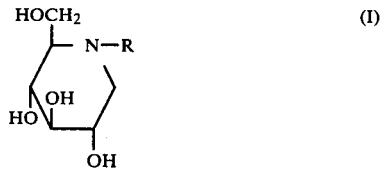

in which

R denotes a hydrogen atom or an optionally substituted alkyl, alkenyl, aralkyl or aryl group, which comprises reacting microbiologically a compound of the general formula

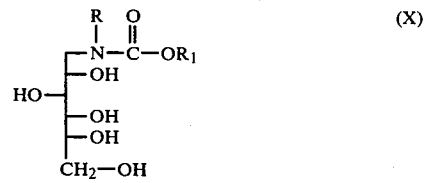

in which

R has the above-mentioned meaning and $R_1$ denotes an optionally substituted benzyl radical or an optionally substituted β-alkenyl group, an aerobic microorganism or an extract of aerobic microorganism capable, in a nutrient medium containing a compound of formula (X), of accumulating an amount of a compound of the formula

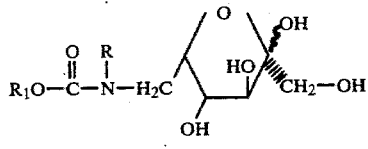

(XI)

in which

R and R₁ have the above-mentioned meanings and subjecting the resulting compound of general formula (XI) to catalytic hydrogenation.

2. A process according to claim 1, in which

R denotes a hydrogen atoms, a $C_1$ to $C_{10}$ alkyl group which is optionally substituted by OH, $C_1$ to $C_4$ alkoxy or di-($C_1$ to $C_4$ alkyl)-amino, or denotes a $C_2$ to $C_{10}$ β-alkenyl group and R₁ denotes a benzyl group which is optionally substituted by chlorine, bromine, nitro, methyl or methoxy, or denotes an allyl group.

3. A process according to claim 2, in which

R denotes a hydrogen atom or a $C_1$ to $C_{10}$ alkyl, hydroxyethyl or allyl group and R₁ denotes a benzyl or allyl group.

4. A process according to claim 1, 2 or 3 in which the microorganism employed is a bacteria of the order Pseudomonadales, coryneform bacteria or a yeast of the order Endomycetales.

5. A process according to claim 1, 2 or 3, in which the micro-organism employed is *Gluconobacter oxydans* ssp. *suboxydans* (DSM 50,049), *Glucobacter oxydans* ssp. *suboxydans* DSM 2003), *Corynebacterium betae* (DSM 20141) of *Metschnikowia pulcherrima* (ATCC 20,515).

6. A process according to claim 3, in which R denotes hydrogen, methyl or hydroxyethyl.

* * * * *